(12) United States Patent  (10) Patent No.: US 7,774,056 B2
Torgerson  (45) Date of Patent: Aug. 10, 2010

(54) DEVICE SITE STIMULATION FOR NOTIFICATION

(75) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 487 days.

(21) Appl. No.: 11/414,533

(22) Filed: Apr. 28, 2006

(65) Prior Publication Data

US 2007/0255339 A1  Nov. 1, 2007

(51) Int. Cl.
*A61N 1/02* (2006.01)
(52) U.S. Cl. ............................................. 607/2; 607/45
(58) Field of Classification Search .................. 607/20, 607/45, 2, 46, 52
See application file for complete search history.

(56) References Cited

U.S. PATENT DOCUMENTS

| | | | |
|---|---|---|---|
| 4,140,131 A | 2/1979 | Dutcher et al. | |
| 4,345,603 A | 8/1982 | Schulman | |
| 5,076,272 A | 12/1991 | Ferek-Petric | |
| 5,411,539 A | 5/1995 | Neisz | |
| 5,549,653 A * | 8/1996 | Stotts et al. .................... | 607/4 |
| 5,578,062 A * | 11/1996 | Alt et al. ........................ | 607/5 |
| 5,607,459 A | 3/1997 | Paul et al. | |
| 5,609,614 A | 3/1997 | Stotts et al. | |
| 5,609,615 A | 3/1997 | Sanders et al. | |
| 5,630,838 A | 5/1997 | Prutchi et al. | |
| 5,709,712 A | 1/1998 | Paul et al. | |
| 6,082,367 A | 7/2000 | Greeninger et al. | |
| 6,397,100 B2 | 5/2002 | Stadler et al. | |
| 6,514,195 B1 | 2/2003 | Ferek-Petric | |
| 6,937,891 B2 | 8/2005 | Leinders et al. | |
| 7,031,773 B1 | 4/2006 | Levine et al. | |
| 7,502,644 B2 * | 3/2009 | Gill et al. .................... | 600/516 |

2001/0051819 A1   12/2001   Fischell et al.

(Continued)

FOREIGN PATENT DOCUMENTS

EP   1 249 254 A2   10/2002

(Continued)

OTHER PUBLICATIONS

U.S. Appl. No. 11/589,698, filed Oct. 30, 2006 entitled: "Inhibition of Stimulation Notification," Torgerson et al.

(Continued)

*Primary Examiner*—Carl H Layno
*Assistant Examiner*—Brian T Gedeon
(74) *Attorney, Agent, or Firm*—Shumaker & Sieffert, P.A.

(57) ABSTRACT

The disclosure is directed to techniques for delivering electrical stimulation for patient notification. An implantable medical device (IMD) may deliver patient notification stimulation via one or more device site electrodes, e.g., electrodes located proximate to an implant site for the IMD, configured as cathodes. Anodes for delivery the patient notification stimulation may be located in an electrode array that is provided by one or more leads and located distally from the implant site, e.g., an electrode array located at one or more target sites for delivery of stimulation therapy. In some embodiments, the IMD may inhibit the patient notification stimulation for a period in response to input from the patient, and then resume the stimulation at the end of the period. In this manner, the notification stimulation may be "snoozed" like an alarm clock. When the stimulation resumes, it may be different, e.g., more urgent, then prior to inhibition.

14 Claims, 6 Drawing Sheets

U.S. PATENT DOCUMENTS

| | | | |
|---|---|---|---|
| 2002/0099412 A1 | 7/2002 | Fischell et al. | |
| 2002/0115940 A1 | 8/2002 | Ferek-Petric | |
| 2002/0120307 A1 | 8/2002 | Jorgenson et al. | |
| 2003/0004552 A1 | 1/2003 | Plombon et al. | |
| 2003/0114899 A1 | 6/2003 | Woods et al. | |
| 2003/0120313 A1 | 6/2003 | Begemann et al. | |
| 2003/0139778 A1 | 7/2003 | Fischell et al. | |
| 2003/0149423 A1 | 8/2003 | Fischell et al. | |
| 2003/0191403 A1 | 10/2003 | Zhou et al. | |
| 2003/0204221 A1 * | 10/2003 | Rodriguez et al. | 607/48 |
| 2004/0172095 A1 | 9/2004 | Jenkins et al. | |
| 2004/0243193 A1 | 12/2004 | Ballis | |
| 2005/0137483 A1 | 6/2005 | Fischell et al. | |
| 2005/0137489 A1 | 6/2005 | Jackson et al. | |
| 2005/0165321 A1 | 7/2005 | Fischell et al. | |

FOREIGN PATENT DOCUMENTS

| | | |
|---|---|---|
| WO | WO 96/32983 | 10/1996 |

OTHER PUBLICATIONS

Notification of Transmittal of the International Preliminary Report on Patentability, dated Apr. 30, 2008 for corresponding PCT Application No. PCT/US2007/001964, (8 pgs.).

Notification of Transmittal of the International Search Report and the Written Opinion of the International Searching Authority, or the Declaration, dated May 31, 2007 for corresponding International Application No. PCT/US2007/001964, (11 pgs.).

Office Action dated Mar. 23, 2009 for U.S. Appl. No. 11/589,698 (12 pgs.).

Responsive Amendment dated Jun. 23, 2009 for U.S. Appl. No. 11/589, 698 (18 pgs.).

Office Action dated Apr. 16, 2010 for U.S. Appl. No. 11/589,698 (11 pgs.).

Responsive Amendment dated Jun. 16, 2010 for U.S. Appl. No. 11/589,698 (16 pgs.).

* cited by examiner

DEVICE SITE STIMULATION FOR NOTIFICATION

TECHNICAL FIELD

The invention relates to implantable medical device and, more particularly, patient notification via implantable medical devices.

BACKGROUND

Implantable medical devices may be used to deliver therapeutic electrical stimulation to patients to treat a variety of symptoms or conditions, such as chronic pain, tremor, Parkinson's disease, epilepsy, cardiac arrhythmia, incontinence, sexual dysfunction, or gastroparesis. In order to treat such symptoms or conditions, an implantable medical device may deliver stimulation via electrical leads that include electrodes located proximate to the "target tissue" for receipt of the stimulation. The target tissue is typically muscle or nerve tissue. As examples, the target tissue may be within or near the spinal cord, heart, cranial nerves, pelvic nerves, gastrointestinal tract, or brain of a patient.

The lead-borne electrodes located proximate to one or more target tissue sites may be referred to as a lead-borne electrode array. In addition to a lead-borne electrode array, many implantable medical devices include device or implant site electrodes, i.e., one or more electrodes proximate to the implantable medical device when implanted relative to the distally-located, lead-borne electrode array. For example, implantable medical devices may use one or more electrodes on their housing, or the housing itself, as an indifferent electrode, i.e., anode, for therapeutic stimulation or other functions.

In general, implantable medical devices deliver stimulation in the form of electrical pulses. At any given time, an implantable medical device may deliver stimulation according to one or more programs, each program including respective values for each of a plurality of stimulation parameters, such as voltage or current pulse amplitude, pulse width, pulse rate and duty cycle. A program may also include an electrode configuration, which identifies electrodes selected for delivery of stimulation and their polarities, i.e., cathode or anode. A group of stimulation parameter values may be referred to as a "program" in the sense that they drive the stimulation therapy to be delivered to the patient.

Implantable medical devices may provide alarms, alerts, reminders or other notifications to a patient for a variety of reasons. As examples, implantable medical devices may provide notifications to a patient for low battery conditions, battery end-of-life conditions, or as a reminder to recharge a battery of the implantable medical device. As other examples, implantable medical devices may provide notifications for lead faults, memory faults, or other device faults. Further, implantable medical devices may provide notifications in response to detected events relevant to the condition of the patient, such as seizures or cardiac arrhythmias, notifications of upcoming therapies, such as defibrillation shocks, or reminders to take concurrent therapies not provided by the implantable medical device, such as one or more drugs. Such notifications are often delivered via audible sounds or tactile vibrations, but in some cases, electrical stimulation has also been used to deliver patient notification.

SUMMARY

In general, the invention is directed to techniques for delivering electrical stimulation for patient notification. During therapeutic stimulation delivery an implantable medical device (IMD) delivers therapy via an electrode configuration in which the one or more cathodes are located within a lead-borne electrode array. The one or more anodes for therapeutic stimulation may also be within the electrode array in the case of bipolar stimulation, or may be device site electrodes, e.g., a housing or housing electrode, in the case of unipolar stimulation.

For patient notification stimulation, the IMD delivers stimulation via an electrode configuration in which the one or more cathodes are device site electrodes, and the one or more anodes are within the lead-borne electrode array. The electrode configuration for patient notification may include any number of cathodes, each of which is a device site electrode, and any number of anodes, each of which is within the lead-borne electrode array. As examples, the electrode configuration for patient notification stimulation may include two or more, or four or more electrodes within the lead-borne electrode array configured as anodes. In some embodiments, all of the electrodes within the lead-borne electrode array are configured as anodes for delivery of patient notification stimulation.

In some embodiments, an IMD may inhibit the patient notification stimulation for a period of time in response to input from the patient. The IMD may then resume the stimulation at the end of the period. In this manner, the patient may "snooze" the notification stimulation, in a manner similar to snooze features in a conventional alarm clock.

When the stimulation resumes, it may be different, e.g., more urgent or intense, than stimulation delivered just prior to the inhibition. For example, stimulation delivered after an inhibition may be delivered according to a different program, which may have a higher pulse amplitude or width. Further, the different program may have a different duty cycle, or provide a different pattern or "rhythm" of stimulation, which is discernable by the patient. In some embodiments, the IMD may allow the patient to inhibit a notification multiple times. Each subsequent inhibition period may be different, e.g., shorter.

In one embodiment, the invention is directed to an implantable medical device comprising one or more device site electrodes located proximate to an implant location for the implantable medical device, a lead-borne electrode array located distally from the implant location, and a processor to control delivery of therapeutic stimulation via a first electrode configuration and patient notification stimulation via a second electrode configuration. The lead-borne electrode array includes each cathode for the first electrode configuration. Further, the one or more device site electrodes include each cathode for the second electrode configuration, and the lead-borne electrode array includes each anode for the second electrode configuration.

In another embodiment, the invention is directed to a method comprising delivering therapeutic stimulation from an implantable medical device to a patient via a first electrode configuration, wherein each cathode of the first electrode configuration is within a lead-borne electrode array located distally from an implant location for the implantable medical device, and delivering patient notification stimulation from the implantable medical device to the patient via a second electrode configuration, wherein each cathode of the second electrode configuration is a device site electrode located proximate to the implant location, and each anode for the second electrode configuration is within the lead-borne electrode array.

In another embodiment, the invention is directed to an implantable medical device comprising one or more device site electrodes located proximate to an implant location for the implantable medical device, and a processor. The processor controls delivery of patient notification stimulation via the device site electrodes to a patient according to a first program, stops delivery of the patient notification stimulation according to the first program in response to an input from the patient, and delivers the patient notification stimulation via the device site electrodes according to a second program following an inhibition period after stopping delivery according to the first program.

In another embodiment, the invention is directed to a method comprising delivering patient notification stimulation from an implantable medical device to a patient via one or more device site electrodes according to a first program, the device site electrodes located proximate to an implant location for the implantable medical device, stopping delivery of the patient notification stimulation according to the first program in response to an input from the patient, and delivering the patient notification stimulation according to a second program following an inhibition period after stopping delivery according to the first program.

In some cases, the invention may be implemented in software of an IMD or other device. Accordingly, the invention may be directed to a computer-readable medium comprising instructions. The instructions may cause a programmable processor to perform any of the methods or techniques described herein. The programmable processor that executes the instructions may be a processor within the IMD or other device.

Embodiments of the invention may provide advantages. For example, by delivering internal stimulation notifications rather than external notifications via a programmer, such as via a programming device, IMDs according to the invention may facilitate patient notification even if the patient has lost the programmer or is not carrying the programmer. By delivering stimulation with cathodes at the device site rather than at a distal, lead-borne electrode array, IMDs according to the invention can also facilitate notification in situations in which stimulation at the distal array is not perceivable or readily perceivable, such as when the electrode array is located on or within the brain of the patient.

Further, IMDs according to the invention may employ the techniques described herein to deliver patient notification stimulation through components typically included as part of implantable medical devices, such as a device housing or housing electrode, and a lead-born electrode array used to deliver electrical therapy to target tissue. In other words, specialized electrodes may not be required for delivery of patient notification stimulation according to some embodiments of the invention.

Additionally, in embodiments in which multiple distal, lead-borne electrodes are used as anodes for patient notification stimulation, the current density at such anodes may be low enough to avoid unintended capture or activation of target tissues or other tissues proximate to the distal electrode array. Further, in embodiments that allow the patient to inhibit the notification, the inhibition may reduce power consumption and improve patient comfort while provide time for the patient to respond to the notification.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
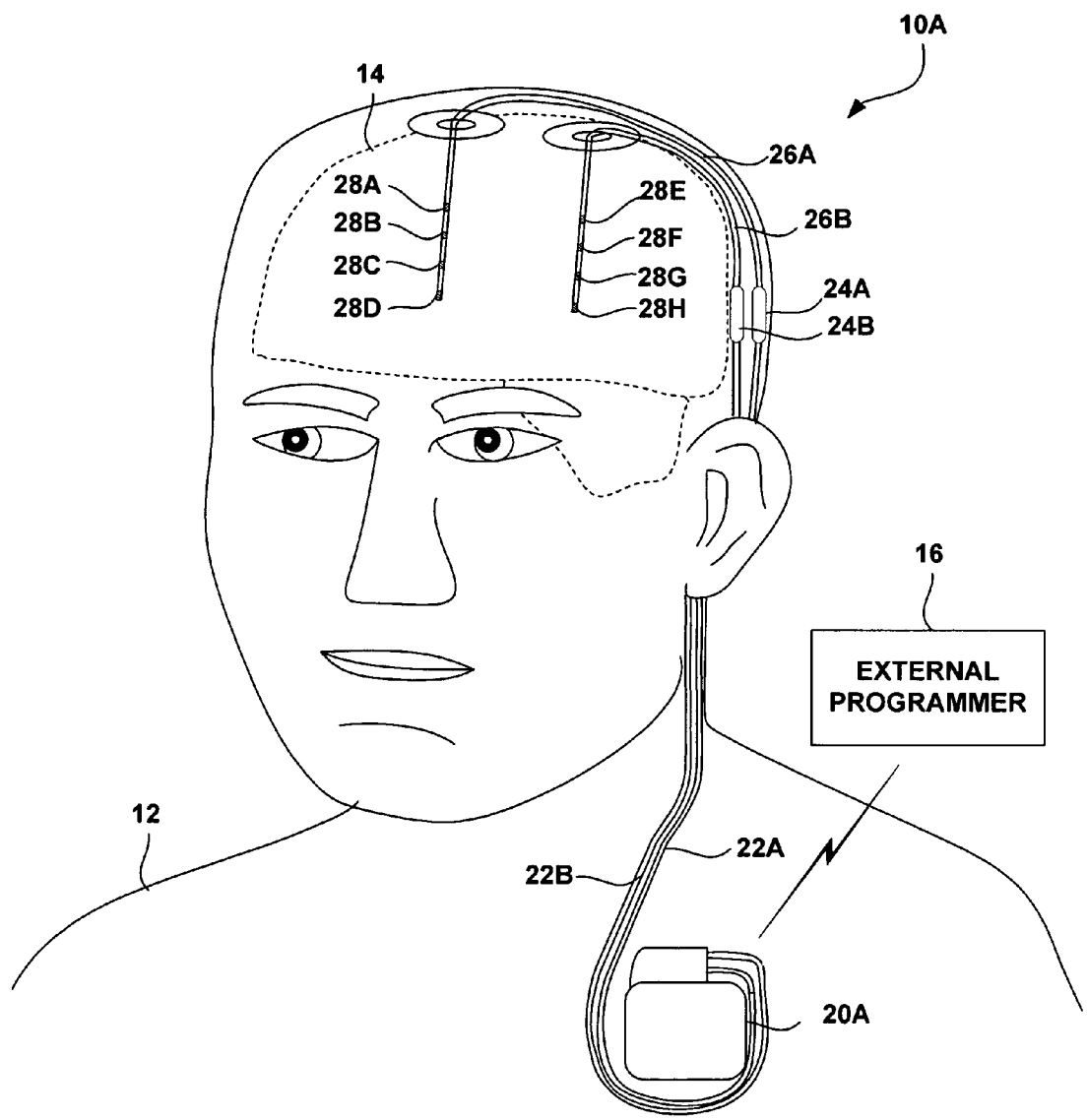
FIGS. 1A and 1B are conceptual diagrams illustrating example systems including example implantable medical devices that deliver device site stimulation for patient notification.
Figure 1B:
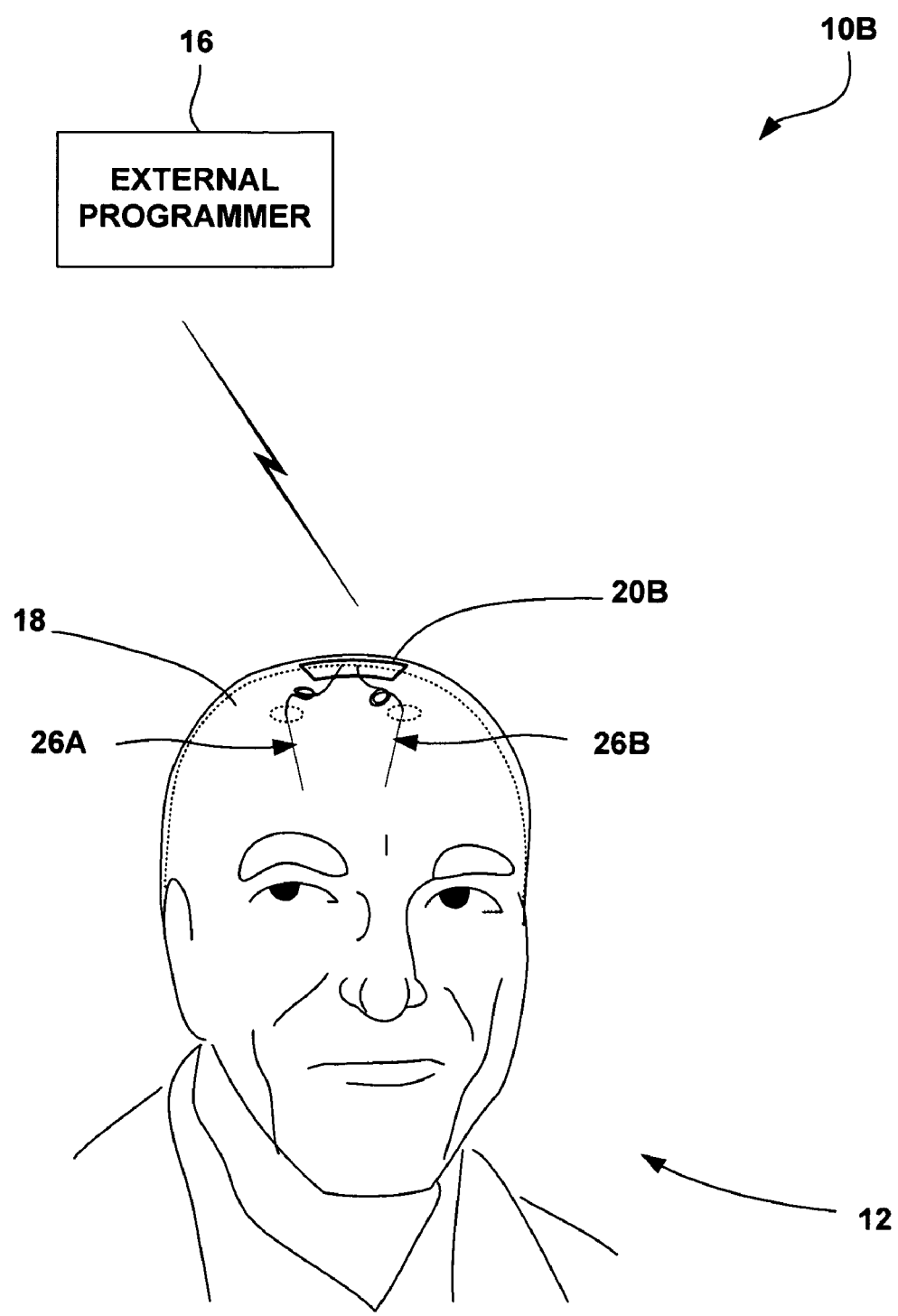

FIGS. 1A and 1B are conceptual diagrams illustrating example systems 10A and 10B (collectively "systems 10") including example implantable medical devices 20A and 20B (collectively "IMDs 20) that deliver device site stimulation to a patient 12 for patient notification. As will be described in greater detail below, IMDs 10 may provide device site stimulation via cathodes located at the device site and anodes located in a distal, lead-borne electrode array, which may facilitate perception of the notification, while avoiding capture or activation of tissue proximate to the electrode array. Additionally, IMDs 10 may allow patient 12 to inhibit the notification, which may reduce battery consumption and increase the comfort of a patient during a period in which the patient is responding to the notification.

As illustrated in FIGS. 1A and 1B, IMDs 20 may be coupled to leads 26A and 26B (collectively "leads 26"), which include electrodes 28A-28H (FIG. 1A) (collectively "electrodes 28") at their distal ends. Leads 26 may be a substantially cylindrical, percutaneously implantable leads, and electrodes 28 may be, for example, ring electrodes. In some embodiments, as illustrated by FIG. 1A, leads 26 may be coupled to IMDs 20 by respective lead extensions 22A and 22B and connectors 24A and 24B.

However, the number, position and configuration of leads 26, electrodes 28, connectors 24 and extensions 22 illustrated in FIGS. 1A and 1B are merely exemplary. IMDs 20 may be coupled to any number of leads, with or without connectors and extensions as necessary or desired, and each lead may include one or more electrodes. Further, leads 26 may have other shapes, such as paddle-like shapes with electrodes located on one or more sides of the paddle, or may include a complex, multi-dimensional electrode array geometry. For example, leads 26 may have a substantially cylindrical shape, and include a plurality of non-ring electrodes located at various circumferential and axial positions thereon. Leads 26 may also include other features, such as fixation elements, to improve tissue growth around the lead in situations where it is desirable to anchor the lead to tissue proximate an implantation site.

FIGS. 1A and 1B also illustrate two example implantation locations for IMDs 20. In particular, FIG. 1A illustrates IMD 20A implanted within the pectoral region of patient 12, while FIG. 1B illustrates IMD 20B cranially implanted, e.g., implanted beneath the scalp of patient 12. IMD 20B may be implanted on cranium 18, or within a recess formed in the cranium of patient 12. The implantation locations illustrated in FIGS. 1A and 1B are merely examples, and IMDs according to the invention may be implanted at any location within a patient.

In the examples illustrated by FIGS. 1A and 1B, leads 26 extend into the brain 14 (FIG. 1A) of patient, and electrodes 28 at the distal ends of leads 26 are located within the brain. IMDs 20 may, for example, deliver deep brain stimulation (DBS) via electrodes 28 to treat any of a variety of symptoms or disorders, such as tremor, Parkinson's disease, epilepsy, or psychological disorders. However, the invention is not limited to DBS or implantation of electrodes 28 within the brain, or delivery of neurostimulation. For example, in other embodiments, electrodes 28 may be implanted proximate to the spinal cord and deliver spinal cord stimulation (SCS) to, for example, treat pain experienced by patient 12. As further examples, one or more leads 16 may be implanted proximate to the pelvic nerves (hot shown) or stomach (not shown), or heart (not shown), and IMD 14 may deliver stimulation therapy to treat sexual dysfunction, incontinence, gastroparesis, cardiac arrhythmias, or a wide variety of other conditions.

As illustrated in FIGS. 1A and 1B, systems 10 may also include an external programmer 16. External programmer 16 allows a user, such as patient 12 or a clinician, to communicate with an IMD 20. External programmer 16 may include a user interface, which may include a display and user input media, such as a touch screen, keypad, or peripheral pointing device, for this purpose. Programmer 16 may be any type of computing device, such as a handheld or tablet computing device. Programmer 16 may communicate with IMDs via wireless telemetry techniques known in the medical device art.

A clinician may use programmer 16 to program stimulation therapy for patient 12, e.g., to create programs including respective values for parameters such as pulse amplitude, pulse width, pulse rate, duty cycle and electrode configuration. The clinician may also use programmer 20 to program patient notification stimulation for patient 12, as will be described in greater detail below. Patient 12 may use programmer 16 to control delivery of therapeutic stimulation by an IMD 20, e.g., select therapeutic stimulation programs or modify parameters of the programs. Patient 12 may also use programmer 16 to inhibit patient notification stimulation, as will be described in greater detail below.

In some embodiments, systems 10 may include multiple programmers 16, e.g., a clinician programmer used by the clinician and a separate patient programmer used by patient 12. Clinician programmers may include more extensive programming capabilities than patient programmers.

Figure 2:
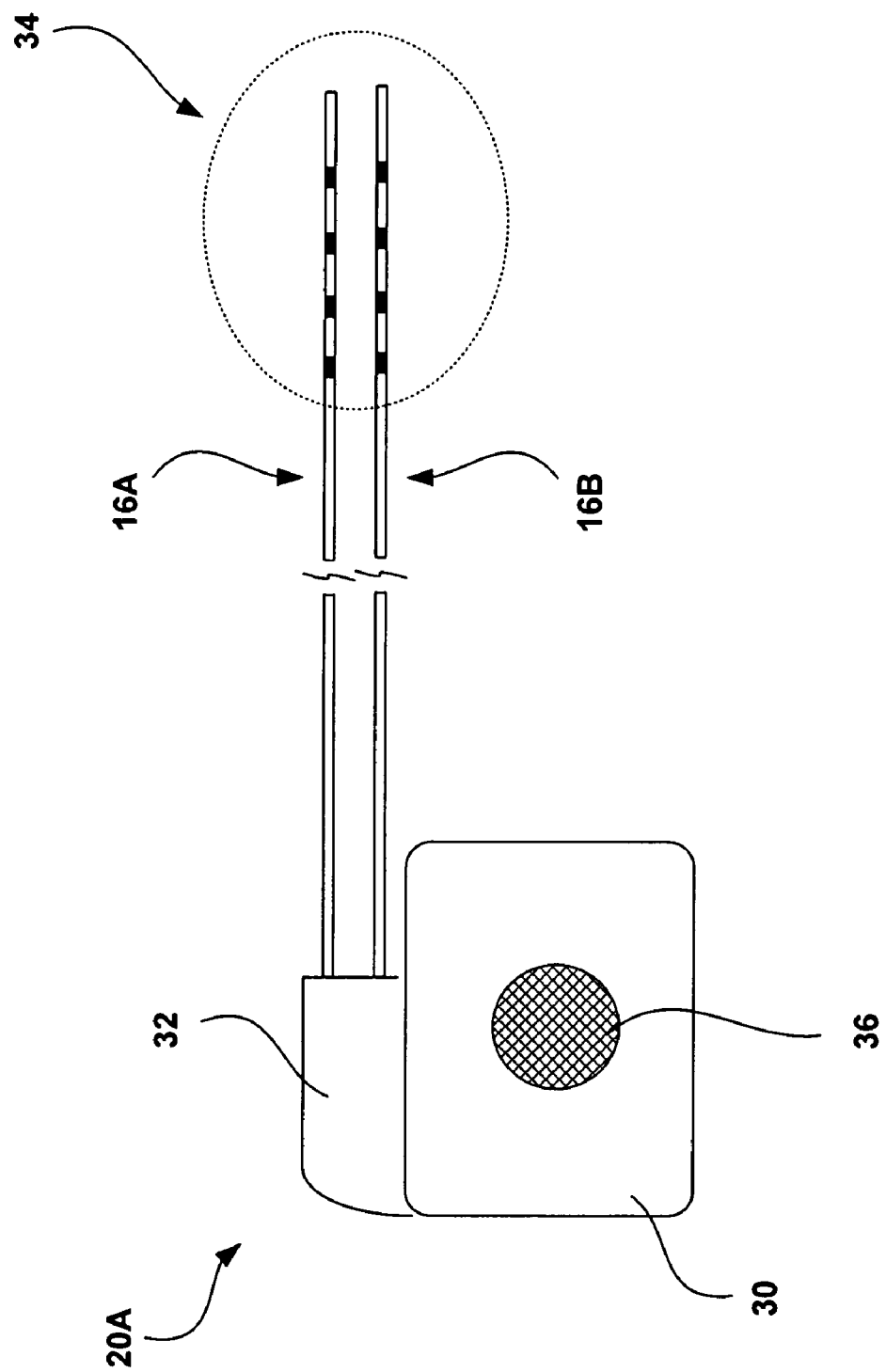
FIG. 2 conceptual diagram illustrating the implantable medical device of FIG. 1A in conjunction with lead-borne electrodes and a device site electrode.

FIG. 2 conceptual diagram illustrating IMD 20A in greater detail. As shown in FIG. 2, IMD 20A may include a housing 30, and a header portion 32 that receives leads 26. Electrodes 28 are shown in FIG. 2 but not labeled for ease of illustration. However, as illustrated in FIG. 2, electrodes 28 collectively form a lead-borne electrode array 34 located distally from housing 30, i.e., distally from the implantation site for IMD 20A. IMD 20A may deliver therapeutic stimulation to target tissue via selected electrodes 28 of array 34.

Further, FIG. 2 illustrates a device site electrode 36 of IMD 20A. In the illustrated example, device site electrode 36 takes the form of an electrode pad formed on housing 30. However, the invention is not limited to the number or configuration of device site electrodes illustrated in FIG. 2. In other embodiments, electrode 36 may be formed on header 32, may be housing 30 itself, or may be coupled to IMD 20A by a significantly shorter conductor or lead relative to leads 26. Although a single device site electrode 36 is illustrated, IMD 20A may include any number of device site electrodes 36, which may be located anywhere on housing 30 or header 32, or otherwise located proximate to the implant site for IMD 20A, i.e., the implant site for housing 30. Further device site electrodes 36 are not limited to the illustrated pad electrode configuration, and may have any shape or configuration.

Although not illustrated in the FIGS., cranial IMD 20B may be coupled to a distal, lead-borne electrode array, and may include a housing, header, and one or more device site electrodes. In cranially-implantable embodiments, one or more device site electrodes may be configured to contact the underside of a scalp of patient 12. For example, the device site electrodes may be located on a side of a housing or header that contacts the scalp.

Figure 3:
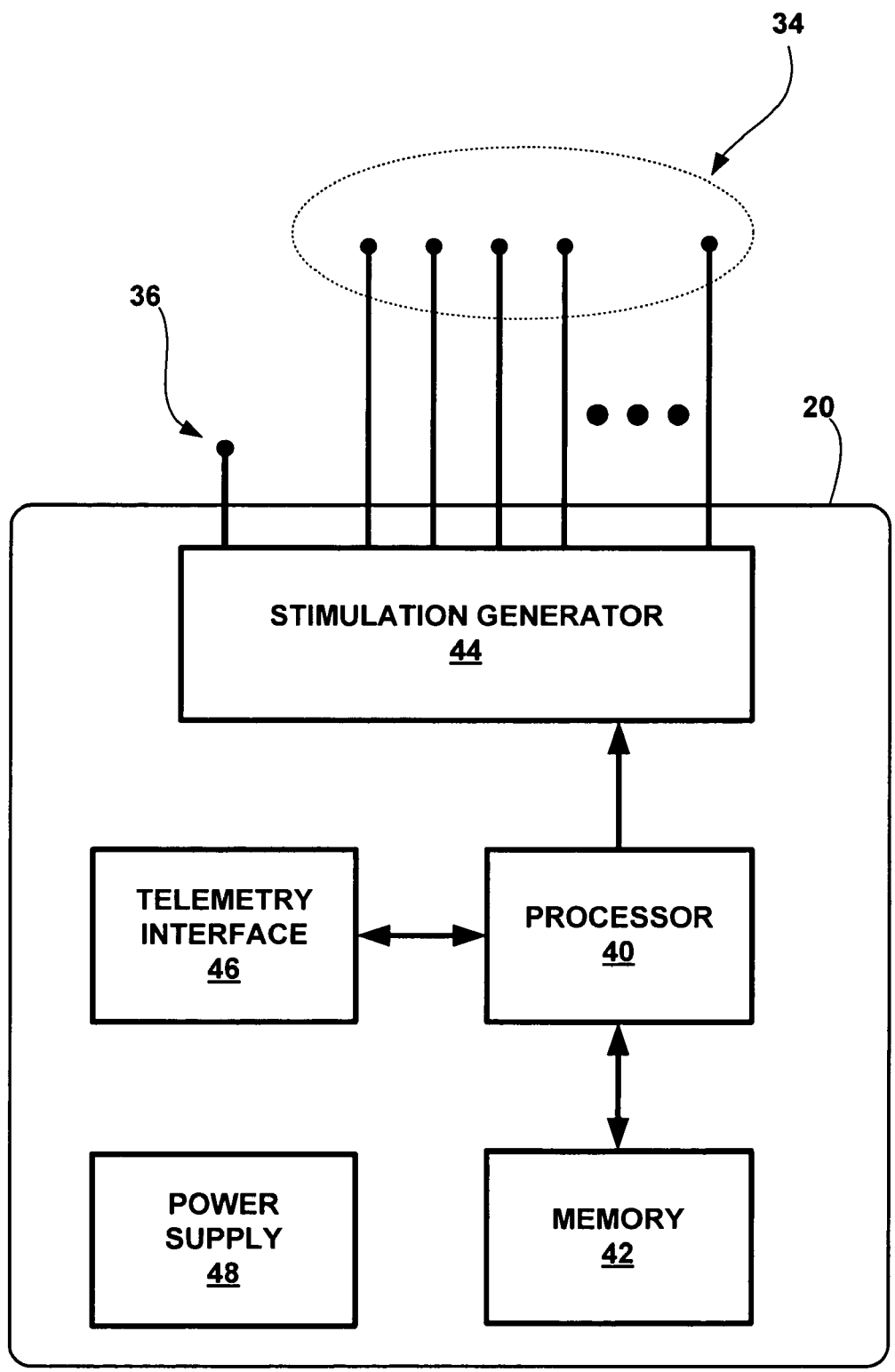
FIG. 3 is block diagram illustrating components of an example implantable medical device that delivers device site stimulation for patient notification.

FIG. 3 is block diagram illustrating example components of an IMD 20 that delivers device site stimulation for patient notification. IMD 20 of FIG. 3 may correspond to either of IMDs 20A and 20B illustrated above. As illustrated in FIG. 3, IMD 20 includes a processor 40, a memory 42, a stimulation generator 44, a telemetry interface 46 and a power supply 48.

Stimulation generator 44 is illustrated as coupled to distal lead-borne electrode array 34 and device site electrode 36. Stimulation generator 44 delivers therapeutic stimulation and patient notification stimulation to patient 12 via selected electrodes with selected polarities from among array 34 and electrode 36 under the control of processor 40. As an example, stimulation generator 44 may include one or more output pulse generation circuits, and switches to control the coupling of the pulse generation circuits to the selected electrodes with the selected polarities.

Processor 40 may control delivery of therapeutic and patient notification stimulation according to programs. The programs for both therapeutic and patient notification stimulation may include values for parameters, such as pulse amplitude, pulse rate, pulse width and duty cycle. The programs may also include an electrode configuration, which may specify selected electrodes from among array 34 and device site electrode 36, and the polarities of the selected electrodes. Further, in the case of patient notification stimulation, the programs may specify a stimulation pattern, which may take the form of a time-varying duty cycle perceivable by the patient as a pattern or rhythm. To the extent patient 12 perceives therapeutic stimulation, the notification stimulation pattern or rhythm may be perceivable by the patient as different from therapeutic stimulation. The programs may have been specified by a clinician using a programmer, and may be stored in memory 42.

In some embodiments, processor 40 inhibits delivery of patient notification stimulation in response to input received from patient. Processor 40 may receive the request may from a programmer via telemetry interface 46. Additionally or alternatively, processor 40 may receive the request via a sensor or switch that detects "tapping" proximate to IMD 20, or the presence or absence of a magnet. Processor 40 may inhibit and resume therapy, which will be described in greater detail below, according to information stored in memory 42, which may have been specified by a clinician using a programmer via telemetry interface 46.

Processor 40 may include may include any one or more of a microprocessor, digital signal processor (DSP), application specific integrated circuit (ASIC), a field-programmable gate array (FPGA), or equivalent discrete or integrated logic circuitry. Memory 42 may store program instructions that, when executed by processor 40, cause processor 40 and IMD 20 to provide the functionality attributed to them herein. Memory 42 may include any volatile, non-volatile, magnetic, optical, or electrical media, such as any one or more of a random access memory (RAM), read-only memory (ROM), non-volatile RAM (NVRAM), electronically-erasable programmable ROM (EEPROM), flash memory, or the like. Telemetry interface 46 may include circuitry to facilitate radio-frequency or inductive telemetry communication with processor 40, as is known in the art. Power supply 48 may be a rechargeable or non-rechargeable battery, or alternatively take the form of a transcutaneous inductive power interface.

Figure 4:
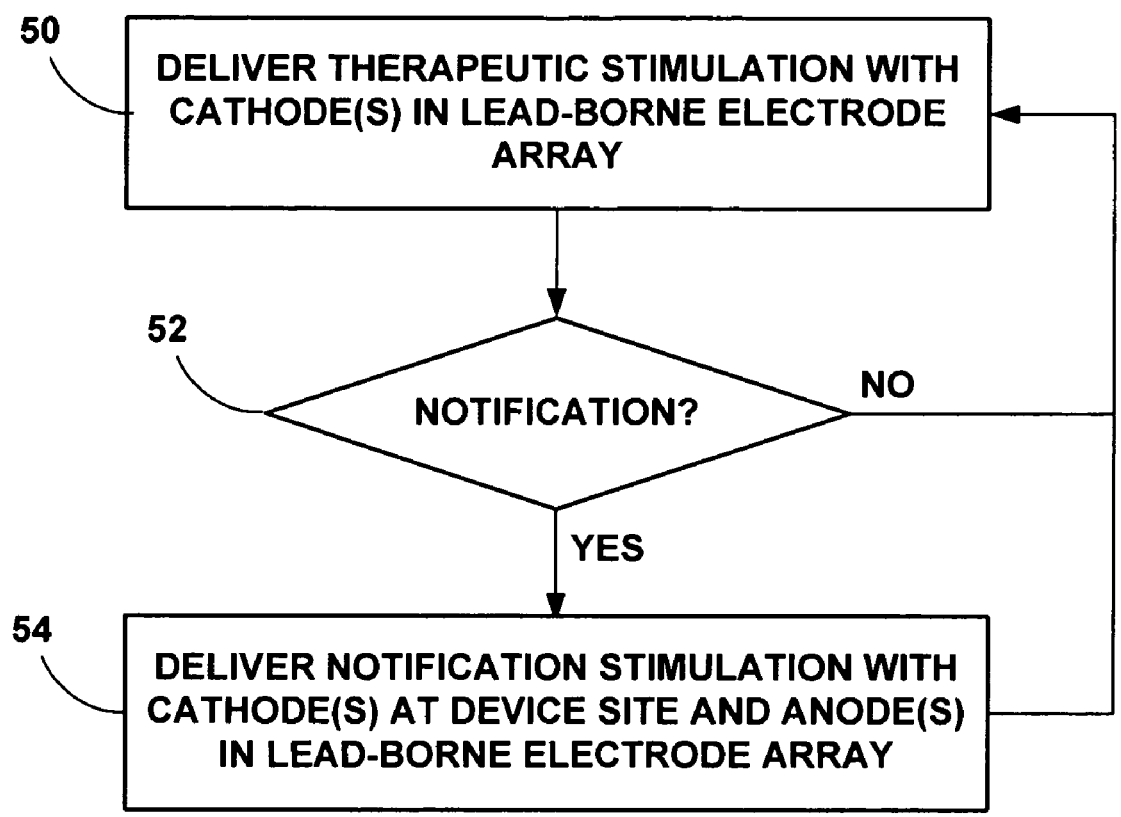
FIG. 4 is a flow diagram illustrating an example method for delivering device site stimulation.

FIG. 4 is a flow diagram illustrating an example method for delivering device site stimulation, which may be executed by IMD 20. According to the example method, IMD 20 delivers therapeutic stimulation via an electrode configuration in which each cathode is included in lead-borne electrode array 34, e.g., as specified by a therapeutic stimulation program (50). One or more anodes for therapeutic stimulation may be located in the electrode array in the case of bipolar stimulation, or may be device site electrodes 36.

IMD 20 may continue to deliver therapeutic stimulation in this manner until the IMD determines that patient notification stimulation should be delivered to patient 12 (52). IMD 20 may deliver patient notification stimulation for alerts, alarms, reminder, or other notifications. As examples, IMD 20 may provide notifications to patient 12 for low battery conditions, battery end-of-life conditions, or as a reminder to recharge a battery of the implantable medical device. As other examples, IMD 20 may provide notifications for lead faults, memory faults, or other device faults. Further, IMD 20 may provide notifications in response to detected events relevant to the condition of the patient, such as seizures or cardiac arrhythmias, notifications of upcoming therapies, such as defibrillation shocks, or reminders to take concurrent therapies not provided by IMD 20, such as one or more drugs.

According to the example method IMD 20 delivers patient notification stimulation via an electrode configuration in which each cathode is a device site electrode, and each anode is within lead-borne electrode array 34, e.g., as specified by a patient notification stimulation program (54). The electrode configuration for patient notification stimulation may include any number of anodes within the array. For example, the electrode configuration for patient notification stimulation may include two or more electrodes, four or more electrodes, or all of the electrodes within array 34 configured as anodes. IMD 20 may deliver patient notification stimulation for a predetermined period of time, until cancelled by patient 12 or a clinician, or until the underlying cause of the notification has been addressed by patient 12 or a clinician. In some embodiments, as will be described below with reference to FIG. 5, IMD 20 delivers patient notification stimulation according methods that facilitate temporary inhibition of the stimulation.

Figure 5:
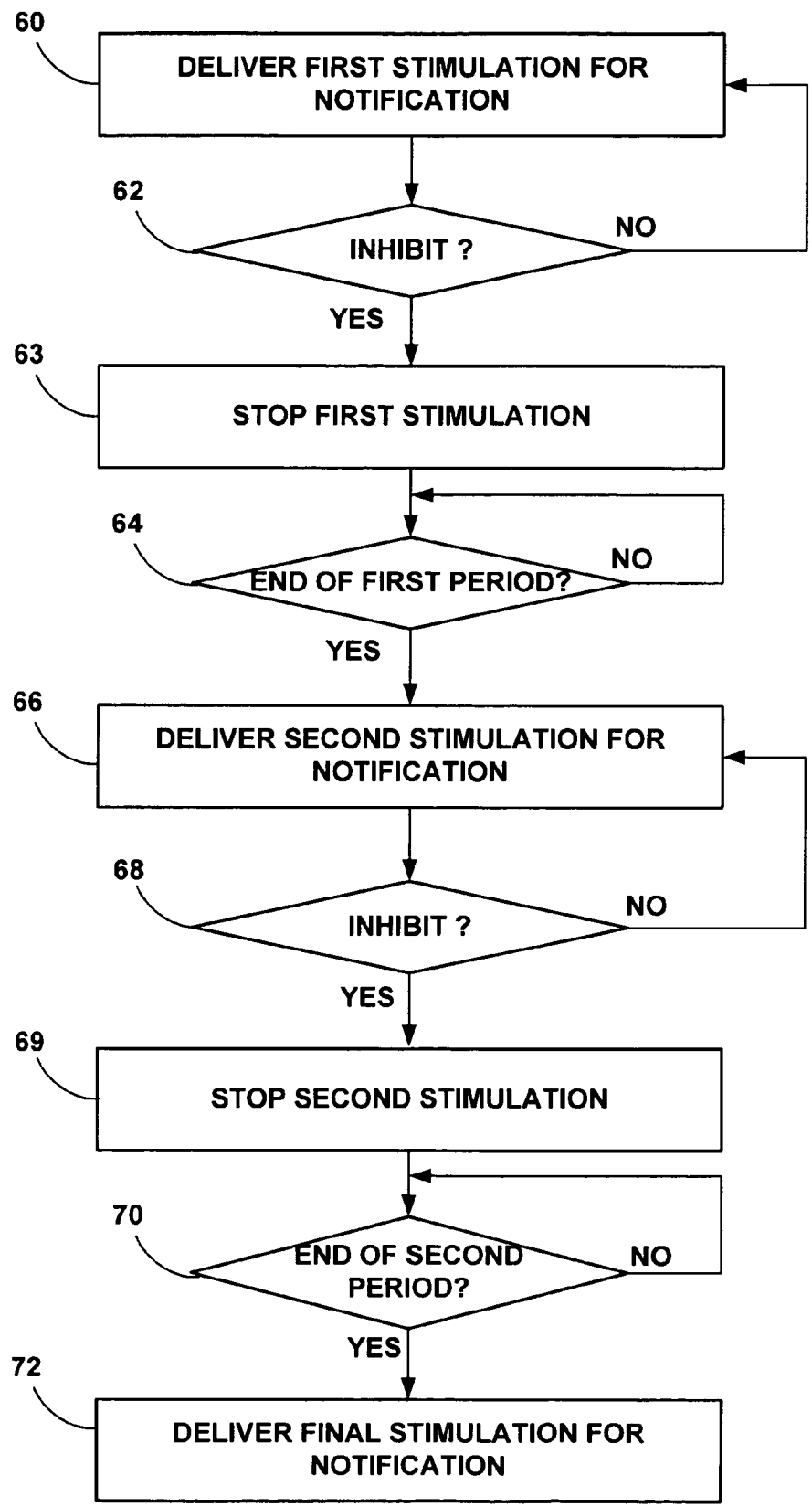
FIG. 5 is a flow diagram illustrating an example method for delivering patient notification stimulation responsive to patient inhibition and including escalating notifications.

FIG. 5 is a flow diagram illustrating an example method for delivering patient notification stimulation responsive to patient inhibition and including escalating notifications. The example method illustrated by FIG. 5 may be practiced by, for example, IMD 20. The delivery of patient notification according to the example method of FIG. 5 may be via device site electrodes and, in some embodiments, via electrode configurations in which each cathode is a device site electrode and each anode is a lead-borne electrode.

According to the example method shown in FIG. 5, IMD 20 delivers first stimulation for patient notification, e.g., delivers stimulation according to a first patient notification stimulation program (60). In response to an input from patient 12 (62), e.g., received via programmer 16, IMD 20 may inhibit or stop delivery of the first patient notification stimulation (63). At the end of a first inhibition period (64), IMD 20 may deliver second stimulation for patient notification (66). The second stimulation may be the same as the first stimulation, or it may be different, e.g., more urgent or intense, then prior to inhibition. For example, stimulation delivered after an inhibition may be according to a second program notification stimulation program, which may have a higher pulse amplitude or width, a different duty cycle, or provide a different pattern or "rhythm" of stimulation, which is discernable by the patient.

In some embodiments, IMD 20 may allow the patient to inhibit a notification multiple times. For example, IMD 20 may deliver the second patient notification stimulation until a second input is received from patient 12 (68). In response to the second input IMD 20 inhibits or stops the second stimulation (69).

At the end of a second inhibition period (70), IMD 20 may deliver a final stimulation for patient notification (72), which may be the same as or different from the previous delivered notifications as described above. IMD 20 is not limited to embodiments that allow two inhibitions as illustrated in FIG. 5, and may allow any number of inhibitions, or no inhibitions. Again, each subsequent inhibition period may be different, e.g., shorter, and each subsequent inhibition stimulation may be different, e.g., more urgent.

In various embodiments, IMD 20 may allow the patient to inhibit all notifications, or only notifications of relatively low urgency. For example, the IMD may allow the patient to initially inhibit low battery or early battery end-of-life notifications. However, the IMD may prevent the patient from inhibiting notifications related to battery conditions or device faults that currently or will imminently comprises the performance of the IMD, e.g., the delivery of therapeutic stimulation. Such notifications may require a relatively immediate response from the patient, such as immediate recharging of the IMD battery, or an immediate visit to a clinic for device reprogramming or replacement. In some embodiments, the IMD may determine the number of times a patient is permitted to inhibit the stimulation notification, the amount of time for each inhibition period, or the urgency of the notification stimulation program used after inhibition dynamically, e.g., based on continuing evaluation of the event or condition that resulted in the notification, or based on a predetermined notification progression. The IMD may select a predetermined notification progression based on the type or urgency of the notification.

Various embodiments of the invention have been described. However, one of ordinary skill in the art will appreciate that various modifications may be made to the described embodiments without departing from the scope of the invention. For example, although described herein in the context of distal, lead-borne electrode arrays that include electrodes used to deliver therapeutic stimulation, the invention is not so limited. In some embodiments, an IMD may additionally or alternatively be coupled to distal, lead-borne electrode arrays that include electrodes not used for therapy, such as electrodes with larger surfaces areas or electrodes not located near target tissue for therapy delivery, which may be used as anodes of patient notification stimulation.

Further, although described herein as being practiced by an IMD, the techniques of the invention may be practiced by other devices, alone or in combination with an IMD. For example, a programming device, such as programmer 16, may identify events or conditions requiring patient notification, and control delivery of patient notification stimulation by IMD according to any of the methods described herein by, for example, providing the IMD commands and/or patient notification stimulation programs. The programming device may be responsive to inputs from the patient to command the IMD to inhibit patient notification stimulation, and may command the IMD to resume patient notification stimulation after an inhibition period.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), flash memory, magnetic media, optical media, or the like. The instructions are executed to support one or more aspects of the functionality described in this disclosure. These and other embodiments are within the scope of the following claims.

The invention claimed is:

1. An implantable medical device comprising:
one or more device site electrodes located proximate to an implant location for the implantable medical device;
a lead-borne electrode array located distally from the implant location; and
a processor to control delivery of therapeutic stimulation via a first electrode configuration and patient notification stimulation via a second electrode configuration,
wherein the lead-borne electrode array includes each cathode for the first electrode configuration, and the one or more device site electrodes are configurable as anodes for the first electrode configuration, and
wherein the one or more device site electrodes include each cathode for the second electrode configuration, and the lead-borne electrode array includes each anode for the second electrode configuration.

2. The implantable medical device of claim 1, further comprising a housing that contains the processor, wherein the one or more device site electrodes include the housing.

3. The implantable medical device of claim 1, further comprising a housing that contains the processor, wherein the one or more device site electrodes include a housing electrode located on the housing.

4. The implantable medical device of claim 1, wherein at least two electrodes within the lead-borne electrode array are anodes for the second electrode configuration.

5. The implantable medical device of claim 1, wherein at least four electrodes within the lead-borne electrode array are anodes for the second electrode configuration.

6. The implantable medical device of claim 1, wherein the lead-borne electrode array is implanted within the brain of the patient.

7. The implantable medical device of claim 1, wherein the implant location is beneath a scalp of the patient, and the device site electrodes are configured to contact the scalp.

8. The implantable medical device of claim 1, wherein the implantable medical device comprises a neurostimulator.

9. A method comprising:
delivering therapeutic stimulation from an implantable medical device to a patient via a first electrode configuration, wherein each cathode of the first electrode configuration is within a lead-borne electrode array located distally from an implant location for the implantable medical device, and one or more device site electrodes located proximate to the implant location are configurable as anodes for the first electrode configuration; and
delivering patient notification stimulation from the implantable medical device to the patient via a second electrode configuration, wherein the one or more device site electrodes include each cathode of the second electrode configuration, and each anode for the second electrode configuration is within the lead-borne electrode array.

10. The method of claim 9, wherein delivering the patient notification stimulation via the second electrode configuration comprises delivering the patient notification stimulation via a housing of the implantable medical device configured as a cathode.

11. The method of claim 9, wherein delivering the patient notification stimulation via the second electrode configuration comprises delivering the patient notification stimulation via a housing electrode located on a housing of the implantable medical device.

12. The method of claim 9, wherein delivering the patient notification stimulation via the second electrode configuration comprises delivering the patient notification stimulation via at least two electrodes within the lead-borne electrode array configured as anodes.

13. The method of claim 9, wherein delivering the patient notification stimulation via the second electrode configuration comprises delivering the patient notification stimulation via at least four electrodes within the lead-borne electrode array configured as anodes.

14. The method of claim 9, wherein the lead-borne electrode array is implanted within the brain of the patient.

* * * * *